United States Patent
Prakash et al.

(10) Patent No.: US 7,030,281 B2
(45) Date of Patent: Apr. 18, 2006

(54) SYNTHESIS OF 3,3,-DIMETHYLBUTYRALDEHYDE BY THE REDUCTION OF 3,3,-DIMETHYLBUTYRIC ACID

(75) Inventors: Indra Prakash, Hoffman Estates, IL (US); Robert L. Augustine, Livingston, NJ (US); Setrak K. Tanielyan, Maplewood, NJ (US)

(73) Assignee: The NutraSweet Company, Chicago, IL (US)

( * ) Notice: Subject to any disclaimer, the term of this patent is extended or adjusted under 35 U.S.C. 154(b) by 0 days.

(21) Appl. No.: 10/390,846

(22) Filed: Mar. 18, 2003

(65) Prior Publication Data

US 2004/0210094 A1    Oct. 21, 2004

Related U.S. Application Data

(60) Provisional application No. 60/366,291, filed on Mar. 21, 2002.

(51) Int. Cl.
*C07C 45/29* (2006.01)
*C07C 29/00* (2006.01)

(52) U.S. Cl. .................. 568/449; 568/448; 568/420; 568/426

(58) Field of Classification Search ............ 568/449, 568/448, 420, 426
See application file for complete search history.

*Primary Examiner*—Elvis O. Price
(74) *Attorney, Agent, or Firm*—Jeffrey M Hoster

(57) ABSTRACT

A process for the production of 3,3-dimethylbutyraldehyde is disclosed. The 3,3-dimethylbutyraldehyde is obtained by the reduction of 3,3-dimethylbutyric acid using trimethylacetic anhydride and a phosphine. The 3,3-dimethylbutyric acid is preferably obtained by a process in which tert-butanol and vinylidene chloride are reacted in the presence of sulfuric acid. The disclosed process has improved cost and yield.

18 Claims, No Drawings

SYNTHESIS OF 3,3,-DIMETHYLBUTYRALDEHYDE BY THE REDUCTION OF 3,3,-DIMETHYLBUTYRIC ACID

This application claims the priority of U.S. Provisional Patent Application Ser. No. 60/366,291, filed Mar. 21, 2002.

BACKGROUND OF THE INVENTION

1. Field of the Invention

This invention relates to the preparation of 3,3-dimethylbutyraldehyde. More particularly, the invention relates to the preparation of 3,3-dimethylbutyraldehyde by the reduction of 3,3-dimethylbutyric acid.

2. Description of the Background Art

U.S. Pat. No. 5,480,668 to Nofre et al. describes high potency sweetening agents comprising N-substituted derivatives of aspartame (L-aspartyl-L-phenylalanine methyl ester). A preferred compound described by Nofre is N-[N-(3,3-dimethylbutyl)-L-α-aspartyl]-L-phenylalanine 1-methyl ester, also known as neotame. The '668 patent describes the production of this compound by the reaction of 3,3-dimethylbutyraldehyde with aspartame in the presence of a reducing agent. Other synthesis methods for the production of neotame also use 3,3-dimethylbutyraldehyde, for example, U.S. Pat. No. 5,728,862 to Prakash.

As 3,3-dimethylbutyraldehyde has not been utilized in commercial quantities, conventional methods for its production have been limited, resulting in its availability only in limited quantities and at very high prices. Recently, a number of processes for the production of 3,3-dimethylbutyraldehyde have been discovered, including processes described in U.S. Pat. No. 5,770,775 to Prakash et al., U.S. Pat. No. 5,973,209 to Prakash et al., U.S. Pat. No. 5,856,584 to Prakash et al., U.S. Pat. No. 5,905,175 to Prakash et al., U.S. Pat. No. 5,994,593 to Prakash et al., and U.S. Pat. No. 5,977,415 to Prakash et al. Each of these processes produces 3,3-dimethylbutyraldehyde having acceptable purity and yields; however, the cost of such processes is such that further cost reductions remain desirable. 3,3-dimethylbutyraldehyde is also prepared by the reduction of 3,3-dimethylbutyric acid by lithium and methyl amine (Bock, et al. J. Am. Chem. Soc. 1974, 96, 2814) and by the Rosenmund reduction of tert-butylacetyl chloride (Collect. Czech. Chem. Commun. 1987, 52, 514). Recently the synthesis of aldehyde by the reduction of acid has been reported in WO 01/38297 using hydrogen, palladium acetate and tri p-tolylphosphine; however, the synthesis of 3,3-dimethylbutyraldehyde from 3,3-dimethylbutyric acid (tert-butylacetic acid) is not described therein.

The synthesis of 3,3-dimethylbutyric acid has been reported, for example, Japanese Patent JP 02-006429 discloses the reaction of isobutylene with vinylidene dichloride and sulfuric acid, followed by hydrolysis. However, this process would have significant cost constraints that would limit its applicability for use as an intermediate for products such as 3,3-dimethylbutyraldehyde.

Thus, there remains a need for a process to produce commercial quantities of 3,3-dimethylbutyraldehyde having acceptable purity and yields, as well as a reduced cost. The present invention provides such a process.

SUMMARY OF THE INVENTION

The present invention describes a process for the production of 3,3-dimethylbutyraldehyde. In the process, 3,3-dimethylbutyraldehyde is formed by reduction of the 3,3-dimethylbutyric acid. The 3,3-dimethylbutyric acid is preferably formed through the reaction of vinylidene chloride and tert-butanol. Then, 3,3-dimethylbutyric acid is converted to 3,3-dimethylbutyraldehyde by the reduction with hydrogen in presence of palladium acetate and tri anisyl-, phenyl-, or tolyl-phosphine.

DETAILED DESCRIPTION OF THE PREFERRED EMBODIMENT

In one preferred embodiment, tert-butanol and vinylidene chloride are reacted in (0.5 to 1.0 mole) in the presence of sulfuric acid to obtain tert-butyl acetic acid. The tert-butylacetic acid is reacted with 1 to 20% Pd(OAc$_2$), hydrogen, trimethylacetic anhydride (0.5 to 1.0 mole of acid) and tri anisyl-, phenyl-, or tolyl-phosphine (1 to 20% of acid) to obtain the end product, 3,3-dimethylbutyraldehyde.

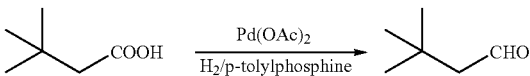

The reaction of the tert-butanol with the vinylidene chloride can be carried out at −30 to 100° C. (preferably −15 to 45° C.) and pressures between atmospheric to 3000 psi (preferably 0–1000 psi).

The reaction is conducted in the presence of an acid, such as sulfuric acid. Sulfuric acid is used in an amount preferably from about 0.5 to 10.0 mole per tert-butanol, most preferably 0.5–1.0 mole per tert-butanol.

The reaction of the tert-butanol with the vinylidene chloride can be performed in a stainless steel or hastalloy vessel to minimize heat transfer limitations. The vessel should be equipped with an agitation system sufficient to ensure good mixing of viscous sulfuric acid mixture. The reaction is preferably conducted in a batch but can also be done using a continuous process. Once the reaction is complete, the mixture can be transferred to a glass vessel for the hydrolysis step due to corrosive nature of dilute sulfuric acid. The hydrolysis of the alkyl disulfate acetal can be performed by adding water to the concentrated sulfuric acid mixture, while controlling the temperature of the reaction mixture. The resulting 3,3-dimethylbutyric acid can be extracted with diethyl ether or other suitable solvent through the use of mixer-settlers, an extraction column, or repeated washing of the acid mixture. The diethyl ether solution can then be dried by passing over a bed of anhydrous sodium sulfate and then distilled or evaporated to recover the acid. The recovery of the 3,3-dimethylbutyric acid can be performed several different ways, including fractional distillation, either batch or continuous, simple distillation of the diethyl ether away from the acid, or through the use of a thin-film evaporator to concentrate the acid. Alternatively, the 3,3-dimethylbutyric acid can be recovered or concentrated as described above, and then dried by passing the concentrated acid over anhydrous sodium sulfate.

The 3,3-dimethylbutyric acid is then reacted with Pd(OAc)$_2$ (0.01 to 50% of acid), and hydrogen, trimethylacetic anhydride (0.5 to 2.0 mole of acid) and tri anisyl-, phenyl-, or tolyl-phosphine (0.01 to 50% of acid) and preferably under the conditions described below. Other palladium, platinum, ruthenium, rhodium metals or their salts and complexes such as carboxylates, halogenides, acetylacetonates, phosphines, acetophosphines, aminophosphines, ferrocenylphosphines can also be used.

Preferably, the hydrogenation is carried out in presence of a tri-p-tolylphosphine as a catalyst modifier. Other modifiers could also be used such as monophosphines (alkyl-, arylalkyl- or aromatic phosphines), di-phosphines (such as bis [diphenylphosphino] alkanes, ferrocenes, benzenes) and arsines.

Instead of trimethylacetic acid anhydride as the dehydrating agent to keep the palladium catalyst in an active form, other drying agents can also be used such as naturally occurring or synthetically obtained molecular sieves. A different approach could also be the use of an intercalated on clay support palladium complex, which will produce a heterogeneous catalyst and a drying agent at the same time.

Good results could be achieved in a number of solvents, including but not limited to, acetone, methyl ethylketone, methyl tert-butylketone, dioxane, tetrahydrofuran, ethyl acetate, methyl acetate, butyl acetate or methyl tert-butyl ether or mixtures of two or more of the above.

The reduction of 3,3-dimethlybutyric acid to produce 3,3 dimethyl butanal can be performed by slurrying Palladium acetate, tolylphosphine and tetrahydrofuran in small reactor, vessel equipped with an agitator and then transferred to the main reactor containing the 3,3-dimethlybutyric acid, acetone and trimethlyacetic anhydride via a pump or vacuum, pressure, or gravity feed system. The mixture is then heated to maintain the desired temperature while under hydrogen pressure. Once the reaction is completed, it is cooled to room temperature and 3,3-dimethylybutyraldehyde can be recovered in several ways, including distillation, fractional distillation, either batch or continuous, or use of a thin-film evaporator to concentrate the 3,3-dimethylbutyraldehyde. The crude 3,3-dimethylbutyraldehyde can be purified as described in U.S. Pat. No. 5,905,175 or by distillation, fractional distillation, either batch or continuous, or use of a thin-film evaporator. A preferred purification step involves distillation at 100–106° C. and atmospheric pressure to obtain purified 3,3-dimethylbutyraldehyde.

The following examples illustrate the present invention in a manner in which it can be practiced, but shall not be construed as limitations on the overall scope of the processes of the invention.

EXAMPLE 1

A 500 mL 3-necked flask was equipped with a mechanical stirrer, an addition funnel and a thermometer. The flask was charged with 100 mL sulfuric acid. Vinylidene chloride (28.2 g) and 15 g tert-butanol were charged into the addition funnel. The flask was cooled to with an ice bath 0–5° C. The mixture of tert-butanol and vinylidene chloride was added to the flask slowly over a period of 30 minutes while maintaining the temperature between 0–5° C. After the addition, stirring was continued for additional 45 minutes. The reaction mixture was poured onto 220 g of crushed ice and extracted with diethyl ether (3×30 mL). The ether layer was dried over anhydrous sodium sulfate, filtered and concentrated under vacuum to give 22 g of 3,3-dimethylbutyric acid as a colorless liquid.

EXAMPLE 2

A Parr autoclave was charged with 7.05 g (60.7 mmol) 3,3-dimethylbutyric acid, 22.8 g (122 mmol) trimethylacetic anhydride and 100 ml acetone. The autoclave was sealed and the air replaced by bubbling nitrogen gas through the solution for 30 min. A separate 25 cc suba-sealed round bottom flask was charged with 137 mg palladium acetate and 930 mg tri-p-tolylphosphine. The air in the flask was removed and replaced by inert gas using three "vacuum—fill with nitrogen" cycles. The solids were later dissolved in 5 cc of degassed tetrahydrofuran, injected into the flask via gas-tight syringe. The RB flask with the suspension was sonicated until the palladium acetate was completely dissolved and the clear solution was later extracted with the same gas-tight syringe and the catalyst solution injected into the autoclave. The reactor was pressurized with hydrogen to 750 psi and the heating was begun at 1000 RPM stirring rate. When the temperature reached 80° C. the monitoring of the hydrogen uptake was started and the reaction was continued for 24 hours. The reactor was cooled to ambient and the solution was passed over 15 g silica for column chromatography. The solution was further concentrated by rot-evaporating the acetone and the pale yellow residue (27.5 g) was collected and analyzed by GC. The concentration of the 3,3-dimethylbutyraldehyde thus determined was 18 mg/ml, which corresponds to 28.8% yield. This mixture was distilled at 100–106° C. to obtain purified 3,3-dimethylbutyraldehyde.

EXAMPLE 3

A Parr autoclave was charged with 7.05 g (60.7 mmol) 3,3-dimethylbutyric acid, 22.8 g (122 mmol) trimethylacetic anhydride and 100 ml acetone. The autoclave was sealed and the air replaced by bubbling nitrogen for 30 min. A separate suba-sealed 25 cc RB flask was charged with 137 mg palladium acetate and 1050 mg tri-p-methoxyphenylphosphine and the air in the flask replaced by three "vacuum—fill with inert gas" cycles. The solids were later dissolved in 5 cc degassed tetrahydrofuran, injected into the flask via gas-tight syringe. The RB flask with the suspension was sonicated until the palladium salt was completely dissolved and the clear solution was later extracted with the same gas-tight syringe and the catalyst solution injected into the autoclave. The reactor was pressurized with hydrogen to 750 psi and the heating was begun at 1000 RPM stirring rate. When the temperature reached 80° C., the monitoring of the hydrogen uptake was started and the reaction was continued for 24 hours. The reactor was cooled to ambient and the solution was passed over 15 g Aldrich silica for column chromatography. The solution was concentrated by rotary-evaporater and 27.5 g pale yellow solution was collected which analyzed by GC shows 4.5 mg/ml 3,3-dimethylbutyraldehyde. This mixture was distilled at 100–106° C. to obtain purified 3,3-dimethylbutyraldehyde.

EXAMPLE 4

A Parr autoclave was charged with 7.05 g (60.7 mmol) 3,3-dimethylbutyric acid, 22.8 g (122 mmol) trimethylacetic anhydride and 100 ml acetone. The autoclave was sealed and the air replaced by bubbling nitrogen for 30 min. A separate suba-sealed 25 cc RB flask was charged with 137 mg palladium acetate and 930 mg of tri-m-tolylphosphine and the air in the flask replaced by three "vacuum—fill with inert gas" cycles. The solids were later dissolved in 5 cc degassed tetrahydrofuran, injected into the flask via gas-tight syringe. The RB flask with the suspension was sonicated until the palladium salt was completely dissolved and the clear solution was later extracted with the same gas-tight syringe and the catalyst solution injected into the autoclave. The reactor was pressurized with hydrogen to 750 psi and the heating was begun at 1000 RPM stirring rate. When the temperature reached 80° C., the monitoring of the hydrogen uptake was started and the reaction was continued for 24 hours. The reactor was cooled to ambient and the solution was passed over 15 g Aldrich silica for column chromatography. The solution was concentrated by rotary-evaporator and 27.5 g pale yellow solution was collected which analyzed by GC shows 9 mg/ml 3,3-dimethylbutyraldehyde. This mixture was distilled at 100–106° C. to obtain purified 3,3-dimethylbutyraldehyde.

What is claimed is:

1. A process for the synthesis of 3,3-dimethylbutyraldehyde, comprising the steps reacting 3,3-dimethylbutyric acid with hydrogen, in the presence of a catalyst, a solvent, dehydrating means and a ligand or catalyst modifier at a temperature and pressure effective to produce 3,3-dimethylbutyraldehyde.

2. The method of claim 1 wherein said catalyst is selected from the group consisting of palladium, platinum, ruthenium, rhodium metals or their salts and complexes selected from the group comprising acetates, carboxylates, halogenides, acetylacetonates, phosphines, acetophosphines, aminophosphines, ferrocenylphosphines.

3. The method of claim 1 wherein said ligand or catalyst modifier is selected from the group consisting of phosphines selected from the group comprising tri anisyl phosphine, phenyl phosphine, and tolyl phosphine.

4. The method of claim 1 wherein said solvent is selected from the group consisting of acetone, methyl ethylketone, methyl tert-butylketone, dioxane, tetrahydrofuran, ethyl acetate, methyl acetate, butyl acetate, methyl tert-butylether or a mixture of thereof.

5. The method of claim 2 wherein said catalyst is palladium acetate.

6. The method of claim 5 wherein said palladium acetate is present in an amount of from about 0.01% to about 50% based on the weight of said 3,3-dimethybutyric acid.

7. The method of claim 3 wherein said phosphine is present in an amount of from about 0.01% to about 50% based on the weight of said 3,3-dimethylbutyric acid.

8. The method of claim 1 wherein said dehydrating means is selected from the group comprising molecular sieves and dehydrating agents selected from the group consisting of anhydrides such as trimethylacetic anhydride and acetic anhydride.

9. The method of claim 1 wherein said reaction is conducted in a reactor which is pressurized at a pressure in the range from 10 psi to 2000 psi.

10. The method of claim 1 wherein said reaction is conducted at a temperature of from about 20 to about 200 degrees Celsius.

11. The method of claim 1 wherein said 3,3-dimethylbutyric acid, said trimethylacetic anhydride and said solvent are charged into a reactor or vessel and sealed prior to addition of said catalyst and said ligand or catalyst modifier.

12. The method of claim 9 wherein bubbling nitrogen is introduced into said reactor.

13. The method of claim 9 wherein hydrogen is charged into said reactor.

14. The method of claim 1 comprising the additional step of purification of the crude 3,3-dimethylbutyraldehyde via distillation, fractional distillation, either batch or continuous or a thin-film evaporator.

15. A method of producing 3,3-dimethylbutyraldehyde comprising the steps of:
   (a) reacting tert-butanol and vinylidene chloride in a vessel in the presence of an acid to produce 3,3-dimethylbutyric acid;
   (b) purifying said 3,3-dimethylbutyric acid using a purification process selected from the group comprising distillation, batch fractional distillation, continuous fractional distillation, or extraction or distillation by means of a thin-film evaporator;
   (c) adding to said vessel hydrogen, in the presence of a catalyst, a solvent, dehydrating agent and a ligand or catalyst modifier at a temperature and pressure effective to produce 3,3-dimethylbutyraldehyde;
   (d) purifying said 3,3-dimethylbutyraldehyde using a purification process selected from the group comprising batch fractional distillation, continuous fractional distillation, or extraction or distillation by means of a thin-film evaporator.

16. The method of claim 15 wherein said vessel is maintained at a temperature of 0 to 5° C. before and during the reaction of tert-butanol and vinylidene chloride.

17. The method of claim 15 wherein said vessel is maintained at a temperature of 50 to 100° C. during the reaction of 3,3-dimethylbutyric acid, hydrogen, ligand or catalyst modifier and catalyst.

18. The method of claim 15 wherein said vessel is maintained at a pressure of 500 to 900 psi during the reaction of 3,3-dimethylbutyric acid, hydrogen ligand or catalyst modifier and catalyst.

* * * * *